United States Patent
Fleming (10) Patent No.: US 8,398,606 B2
(45) Date of Patent: Mar. 19, 2013

(54) FOLDED PERINEAL PAD

(75) Inventor: William H. Fleming, Tualatin, OR (US)

(73) Assignee: QuantrRx Biomedical Corporation, Portland, OR (US)

( * ) Notice: Subject to any disclaimer, the term of this patent is extended or adjusted under 35 U.S.C. 154(b) by 376 days.

(21) Appl. No.: 12/529,053

(22) PCT Filed: Feb. 28, 2008

(86) PCT No.: PCT/US2008/055346
§ 371 (c)(1),
(2), (4) Date: Aug. 28, 2009

(87) PCT Pub. No.: WO2008/106610
PCT Pub. Date: Sep. 4, 2008

(65) Prior Publication Data
US 2010/0030189 A1    Feb. 4, 2010

Related U.S. Application Data

(60) Provisional application No. 60/892,114, filed on Feb. 28, 2007.

(51) Int. Cl.
*A61F 13/20* (2006.01)
(52) U.S. Cl. ............ 604/385.17; 604/385.18; 604/11; 604/14; 604/904
(58) Field of Classification Search ........... 604/385.17, 604/385.18, 11, 14, 904
See application file for complete search history.

(56) References Cited

U.S. PATENT DOCUMENTS

| | | |
|---|---|---|
| 2,092,346 A | 9/1937 | Arone |
| 3,905,372 A | 9/1975 | Denkinger |
| 3,983,873 A | 10/1976 | Hirschman |
| 4,175,561 A | 11/1979 | Hirschman |
| 4,374,522 A | 2/1983 | Olevsky |
| 4,920,045 A | 4/1990 | Okuda et al. |
| 5,045,447 A | 9/1991 | Minson |
| 5,094,956 A | 3/1992 | Grow et al. |
| 5,124,252 A | 6/1992 | Guerrant et al. |
| 5,190,881 A | 3/1993 | McKibbin |
| 5,283,171 A | 2/1994 | Manos et al. |
| 5,447,839 A | 9/1995 | Manos et al. |
| 5,459,034 A | 10/1995 | Tabaqchali et al. |
| 5,538,851 A | 7/1996 | Fach et al. |
| 5,563,071 A | 10/1996 | Augurt |
| 5,580,907 A | 12/1996 | Savin |
| 5,627,275 A | 5/1997 | Roll |

(Continued)

FOREIGN PATENT DOCUMENTS

| | | |
|---|---|---|
| EP | 0423330 | 4/1991 |
| EP | 1064901 | 1/2001 |

(Continued)

OTHER PUBLICATIONS

International Search Report from PCT/US2008/055346 dated Jun. 18, 2008.

(Continued)

*Primary Examiner* — Jacqueline F. Stephens
(74) *Attorney, Agent, or Firm* — Klarquist Sparkman, LLP (57) ABSTRACT

A multi-layered, absorbent perineal pad is disclosed that has a generally ovate cross-section. In disclosed embodiments, the pad has an absorbent outer layer, antimicrobial intermediate layer, and absorbent inner layer. At least two opposing edges of the pad are sealed to one another so that the absorbent inner layer encloses an internal cavity within the pad. The pad may be used to absorb liquids from perineal structures (such as vaginal or anal liquids) or administer agents to perineal structures. Liquids that are absorbed in the pad can be subjected to diagnostic assays.

40 Claims, 3 Drawing Sheets

U.S. PATENT DOCUMENTS

| | | | |
|---|---|---|---|
| 5,661,010 A | 8/1997 | De Lourdes Muñoz Moreno |
| 5,705,332 A | 1/1998 | Roll |
| 5,783,412 A | 7/1998 | Morris et al. |
| 5,876,922 A | 3/1999 | Orth et al. |
| 5,965,375 A | 10/1999 | Valkirs |
| 6,138,500 A | 10/2000 | Steger et al. |
| 6,174,293 B1 | 1/2001 | Buck et al. |
| 6,270,486 B1 | 8/2001 | Brown et al. |
| 6,409,713 B1 | 6/2002 | Osborn, III et al. |
| 6,409,714 B2 | 6/2002 | Osborn, III et al. |
| 6,416,501 B2 | 7/2002 | Brown et al. |
| 6,811,549 B2 | 11/2004 | Fleming |
| 7,033,342 B2 | 4/2006 | Mizutani et al. |
| 7,074,214 B2 | 7/2006 | Mizutani |
| 2005/0182376 A1 | 8/2005 | Fleming |

FOREIGN PATENT DOCUMENTS

| | | |
|---|---|---|
| WO | WO 98/06365 | 6/2005 |
| WO | WO 2005/058219 | 6/2005 |

OTHER PUBLICATIONS

Written Opinion of the International Searching Authority from PCT/US2008/055346.

FIG. 7 ined between the inner and outer absorbent layers, folding the pad such that portions of the inner absorbent layer contact one another, and securing the pad in the folded configuration to form the internal cavity within the pad and between the contacting portions of the inner absorbent layer.

FOLDED PERINEAL PAD

CROSS REFERENCE TO RELATED APPLICATIONS

This is the U.S. National Stage of International Application No. PCT/US2008/055346, filed Feb. 28, 2008, which was published in English under PCT Article 21(2), which in turn claims the benefit of U.S. Provisional Application No. 60/892,114, filed Feb. 28, 2007, which is incorporated by reference herein in its entirety.

PRIORITY CLAIM

This application claims the benefit of U.S. Provisional Application No. 60/892,114, filed Feb. 28, 2007, which is incorporated by reference herein in its entirety.

FIELD

The invention is related to an absorbent pad. The perineal pad is suitable for insertion and retention in a perineal space, such as the interlabial space or intergluteal space. The pad may be used for a variety of purposes, such as catamenial use, incontinence purposes, hemorrhoid treatment, collecting biological material for diagnostic assays, and administering therapeutic agents.

BACKGROUND

A variety of catamenial devices has been used to collect vaginal discharges such as menstrual fluid. One such device is a sanitary napkin that is configured to be externally worn in the perineal region. An alternative to the sanitary napkin is a tampon which fits internally within the vaginal cavity to interrupt the external flow of menstrual blood. Hybrid devices that merge the structural features of sanitary napkins and tampons have also been proposed, as shown in U.S. Pat. Nos. 2,092,346 and 3,905,372.

An interlabial pad is a more recent catamenial device that provides greater convenience because of its small size. Examples of interlabial pads are shown in U.S. Pat. Nos. 3,983,873 and 4,175,561 that issued to A-Fem Medical Corporation (now known as QUANTRX® Biomedical Corporation) of Portland, Oreg. The interlabial pad has grown in popularity in recent years, as evidenced by many other patents that have issued on these pads, such as U.S. Pat. Nos. 6,270,486; 6,409,713; 6,409,714; 6,416,501; 7,033,342; and 7,074,214.

Another advantageous use of interlabial pads has been in the local or systemic administration of therapeutic agents. As disclosed in U.S. Pat. No. 6,811,549, it has been found that the interlabial pads provide targeted delivery of drugs for local and transdermal administration. The permeability of the labial area to many drugs (such as hormones, for example estrogen) has made the pads ideal drug delivery devices even for systemic disorders. However they are also advantageous in the targeted treatment of labial and peri-labial infection inflammation or in the retention of intravaginally delivered drugs.

Interlabial pads can also function as diagnostic collection devices. For example, U.S. Pat. No. 6,174,293 disclosed that interlabial pads could be applied externally to collect vaginal fluid and vaginal cells for subsequent diagnostic analysis. This collection technique was noted to be useful in the laboratory evaluation of tumors (such as vaginal cancer), infectious disorders (such as sexually transmitted diseases), hormone levels, and the detection of drugs of abuse.

Absorbent pads have also been used in the treatment of urinary incontinence, for example by collecting small amounts of liquid discharged by a subject who has stress incontinence. More recently the use of self-retained pads has been provided for the treatment of anal conditions, such as hemorrhoids, or for absorbing anal leakage, as in published U.S. Patent Publication 2005/182376.

Although the use of interlabial pads represents a significant advance in the field, existing interlabial pads have sometimes interfered with diagnostic assays. The materials some pads are made of can disrupt cellular structures that are collected for pathological examination (for example in a Pap smear). Some collection pads are also susceptible to bacterial overgrowth during storage and shipment, or contain materials that bind cells and other biological materials of diagnostic interest.

Another problem with some prior pads is that they have a low density core that wicks fluid to the center of the pad such that the fluid distributes itself preferentially in the absorbent material long the length of the pad. This distribution tends to cause the pad to leak from its ends.

One object of certain embodiments of the current disclosure is to provide a perineal pad that, in addition to serving as a catemenial, urine collection or drug delivery device, is also useful in the collection of liquids (such as vaginal or anal liquids) for diagnostic analysis.

The disclosed device is also suitable for the perineal (for example interlabial or anal) administration of therapeutic substances for direct topical or transdermal delivery.

SUMMARY

Multiple embodiments of an interlabial device are disclosed herein for catamenial and incontinence purposes, collection of fluids and/or cells for diagnostic analysis, and administration of therapeutic substances.

A method is disclosed for collecting biological liquid from a subject. A multiple layer absorbent pad is provided that is of a size that is suitable for retention in a perineal space of a wearer (such as an intergluteal or interlabial space). The pad includes an inner absorbent layer, an outer absorbent layer, and an intermediate layer between the first and second absorbent layers. The inner and outer layers are denser than the intermediate layer. An empty internal cavity is present in the pad, so that liquid that enters the internal cavity is absorbed through the inner absorbent layer into the intermediate layer, and liquid external to the device is absorbed through the outer absorbent layer into the intermediate layer. The lower density of the intermediate layer promotes the retention of liquid in the intermediate layer instead of in the cavity within the pad.

In certain embodiments, the intermediate layer is substantially thicker than the inner and outer layers. In some embodiments, the intermediate layer comprises at least 50% of the thickness of a wall of the pad (wherein the wall includes the inner and outer layers and the intermediate layer). In other embodiments, the thickness of the inner layer is less than 10% or 5% of the thickness of the pad, and the thickness of the outer layer is less than 10% or 5% of the pad. The intermediate layer can be made of a low density material such as rayon or fibrous cellulose or silk that serves as a reservoir for the liquid. The softness and low density of the rayon or silk improves the comfort of the pad when it is retained in the perineal space.

The internal cavity of the pad can be formed by providing a pad of material having the intermediate layer contained between absorbent layers. The pad has a top edge and a bottom edge that can be secured to one another to enclose the internal cavity, while leaving the ends of the pad unsecured so that liquid from the cavity can flow out of the cavity through the open ends. Loss of the liquid through the open ends is inhibited by absorption of liquid from the cavity into the intermediate lower density layer.

In one embodiment, the device includes a multiple layer absorbent pad capable of insertion, including placement within, and retention in the interlabial space of a female wearer. The multiple layers of the pad include at least one absorbent layer and an intermediate layer, such as an anti-microbial layer. In disclosed embodiments, the intermediate layer is one or more of thicker and/or less dense than the absorbent layer. The pad has a length, width, thickness, a longitudinal centerline and opposing top and bottom edges. The pad is folded along the longitudinal centerline with the opposing top and bottom edges secured to one another to present the absorbent layer externally of the intermediate layer. The pad forms an internal cavity (empty area) that does not contain absorbent material, and avoids the wicking of fluids into the center of the pad and along its length that would otherwise promote leakage from the ends of the pad.

The pad may also include an absorbent inner layer that faces the cavity to absorb liquid back into the pad material itself so that the liquid is more evenly distributed throughout the device. Interposing the less dense intermediate or anti-microbial layer between two more absorbent layers also helps preferentially retain any liquid in the intermediate layer. In this embodiment, liquid in the internal cavity is absorbed through the inner absorbent layer into the intermediate layer and liquid external to the device is absorbed through the outer absorbent layer into the intermediate layer. Although these forces exist in equilibrium, the overall effect is a tendency for liquid to be retained in the intermediate layer.

In certain embodiments, the intermediate layer is made of an anti-microbial fiber, such as rayon or silk, which inhibits the growth of bacteria. Fibers such as rayon have been found to have inherent anti-microbial activity. The anti-microbial intermediate layer forms a non-external layer of the device that is sandwiched between two absorbent layers.

When the pad is folded to form the interlabial device, one absorbent layer forms the wall of the internal cavity, another absorbent layer forms an external surface of the device, and the intermediate layer is contained between the absorbent layers. The intermediate layer may be of a lower density material than the adjacent absorbent layers, such that fluid preferentially collects in the intermediate layer. The preferential accumulation of the liquid in the intermediate layer helps inhibit the collection of liquid in the cavity, and thereby reduces leakage of the liquid from the ends of the device. In those embodiments in which the intermediate layer is an anti-microbial layer, the collection of liquid in the intermediate layer reduces bacterial growth during collection and/or storage and/or shipment of liquid samples (for example to a laboratory for analysis).

In other examples, a flap extends from a transverse edge of the absorbent pad, and the flap is folded against the pad so that the flap is contained within the internal cavity. The folded edge facilitates manufacturing of the device, and forms a softer leading edge that can be placed adjacent the sensitive urethral meatus.

In disclosed examples, the device when folded has a transverse cross-sectional profile that is wider at the folded longitudinal centerline than at the edges that are secured to one another along the bottom of the device. The device can assume a generally ovate or egg-shaped transverse cross-sectional profile that is wider at the folded longitudinal centerline that is placed against the body and narrower at the edges that are secured to one another. When folded, the device can have substantial smooth sides, for example to present a substantially smooth surface area for contact with the wearer's skin. Thus, in some examples the folded pad has substantially smooth outer surfaces, for example the outer surface does not contain any grooves or channels. In some disclosed examples, the pad is non-adhesive, such that it does not adhere to the skin and/or a supporting garment, for example it does not have an adhesive surface, such as a surface that has applied adhesive or has been rendered adhesive.

The device may be used in methods of collecting vaginal fluid and/or exfoliated vaginal cells contained in the fluid for diagnostic purposes. Certain examples of such methods include placing the device in the interlabial space; collecting liquid in the device while the device is located in the interlabial space; removing the device and extracting liquid from it; then performing medical diagnostic testing on the extracted liquid.

The liquid can contain cells such as ectocervical, cervical, endometrial, vaginal or blood cells. Diagnostic testing can include, for example, testing for bacterial, viral and parasitic diseases, such as gonorrhea, syphilis, trichomonas, chlamydia, candida, papillomavirus, herpes, gardnerella and acquired immunodeficiency syndrome (AIDS). Alternatively, the testing can be directed toward the detection of neoplastic disorders, such as cancers. A variety of testing techniques can be used, such as immunochemical, physical, or microscopic examination of the extracted material.

The liquid from the absorbent medium can be placed in a liquid extraction medium that contains preservatives and buffers. The extracted liquid can be placed in a shipping container for shipment to a diagnostic center for analysis. However the pad itself can be shipped with the liquid still in it. An anti-microbial layer in the pad helps avoid microbial growth during transshipment.

Alternatively the device can be used for catemenial purposes, or collection of urine, for example in a subject having stress incontinence. In yet other embodiments it is a drug delivery device, delivering a drug retained either in the absorbent material of the pad or from the internal cavity formed within the device.

Methods of making the device are also disclosed, for example by folding the multi-layered pad along its longitudinal centerline and securing opposing top and bottom edges of the pad to each other. In certain embodiments in which the flap extends from one transverse edge, the flap is folded against an interior face of the pad before the pad is folded along it longitudinal centerline. The top and bottom edges of the pad are then secured to one another to form the device.

The foregoing and other objects, features, and advantages of the invention will become more apparent from the following detailed description, which proceeds with reference to the accompanying figures.

BRIEF DESCRIPTION OF THE DRAWINGS

FIGS. 9A-9E schematically illustrate the method of making a second embodiment of the device.

DETAILED DESCRIPTION

As used herein, an "absorbent perienal device" refers to a structure that has at least some absorbent components, and which is specifically configured to reside at least partially within a perineal space, such as an interlabial space of a female wearer or an intergluteal space adjacent the anus of a wearer of either gender.

"Absorbent" refers to a material with sufficient absorbency to absorb and retain exudates or other liquids discharged from a subject. Absorbency is dependent partially on the physical volume of the device. In a specific non-limiting example, a material is absorbent if it absorbs at least 3 ml of 0.9% saline, but an absorbent material may have a capacity of 20 grams or more.

An "agent" is a substance capable of producing a physical, chemical or biological effect. A "medicinal agent" produces a medical effect. Examples of agents include drugs (therapeutic agents) and diagnostic reagents (diagnostic agents). Examples of drugs include antimicrobial agents (such as the anti-fungal agent miconozole, anti-viral acyclovir, or anti-biotic metronidazole), as well as anesthetics and lubricants. Examples of diagnostic agents include monoclonal antibodies, such as monoclonal antibodies that recognize human papillomavirus (HPV) or herpes simplex virus (HSV), or chemical reagents in which a reaction occurs in the presence of a pathogen of interest (such as a color change).

A "biodegradable material" has greater than or equal to about 70% biodegradation (percentage of theoretical carbon dioxide evolution) after 28 days when measured by a suitable test such as the Sturm test (Method 301B, Organization of Economic Cooperation and Development). The devices disclosed herein may be made of biodegradable material.

Figure 3A:
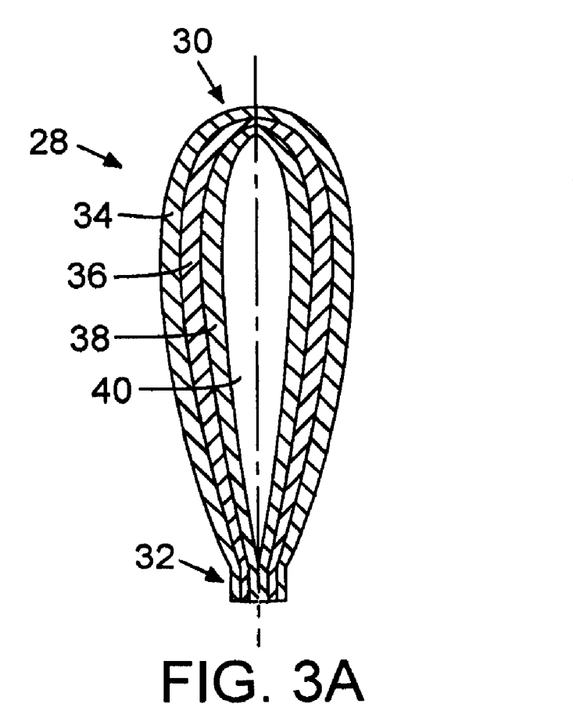
FIGS. 3A and 3B are alternative cross-sectional views of the new interlabial device described herein.
Figure 3B:
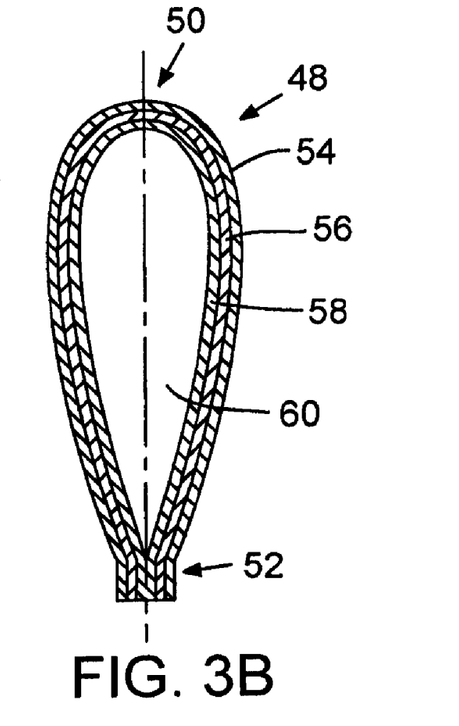

A "cavity" is a space, enclosure or sinus surrounded by something, such as an absorbent pad. The cavity does not contain the surrounding material, but can instead be occupied by air or a therapeutic or diagnostic substance. The cavity can be two-dimensional (for example, circumscribed in a two-dimensional cross-section as in FIGS. 3A and 3B) or three-dimensional (completely enclosed by surrounding material). The cavity in disclosed examples is formed by an elongated pad that is folded over, with opposing faces of the pad secured to one another (for example along edges of the pad). The resulting internal cavity is surrounded in a transverse plane by the absorbent material, although the disclosed cavity communicates with the environment outside the cavity through open ends of the cavity. The cavity is capable of receiving liquid samples from the environment, and retaining at least temporarily before they are reabsorbed in to the absorbent layers of the pad. A cavity is larger than and is not a pore, and in disclosed embodiments the cavity has a potential volume of at least 2 ml, 9 ml or 15 ml. In particular embodiment, the potential volume of the cavity is 2-9 ml. The potential volume of the cavity refers to a volume of the cavity before it is compressed and reduced in size by surrounding tissue during use. The cavity in its fully expanded dimension need not be regular or symmetric in shape, although depicted examples of the cavity in FIGS. 3 and 9 show a symmetric void that is elongated both longitudinally in two dimensions (longitudinally along the pad and in height). An "internal cavity" differs from an "external cavity" which is a surface defect in an object. In disclosed examples, an internal cavity is circumscribed in at least one plane by the material that forms the cavity.

The "density" of a fiber refers to its mass per unit volume, as expressed in units such as $g/cm^3$. A lower density material has a lower mass per unit volume than a reference material. In the disclosed examples, the intermediate layer of the pad may have a lower density than the more absorbent layers between which it is sandwiched. The lower density material is capable of acting as a better reservoir for liquid that is transmitted to it through the absorbent layers, and the reservoir provided by the lower density material helps promote an equilibrium state in which liquid is preferentially retained in the less dense intermediate layer as compared to the adjacent absorbent layers. The density of material in a layer of the pad can be determined by the average fiber density in that layer. The "average fiber density" of a region refers to the average fiber density of the fibers in the region. The average fiber density may be measured using Micro Cat Scan or Resin Embedded Microtome along with Scanning Electron Microscopy—S.E.M. (supplied by companies such as Resolution Sciences Corporation; Corte Madera, Calif.).

A "diagnostic test" is any assay performed on a sample collected from a subject, wherein the procedure can be used to evaluate or monitor a disease or a disorder in the subject. A diagnostic test can be performed in a laboratory, a medical office or in the home environment.

The "gluteal region" is an anatomical region bounded superiorly by the iliac crest and inferiorly by the fold of the buttock. The region is largely made up of the gluteal muscles and a thick layer of superficial fascia.

The "intergluteal space" is the space located between the right and left gluteals (buttocks), generally on a sagittal plane that includes the anus. The intergluteal space extends inferiorly toward the perineum to the vaginal opening in the female (but does not include the vaginal opening), and toward the scrotum in the male (without including the scrotum). The anus is located in the intergluteal space, and the pads disclosed herein can be retained in the intergluteal space against the anal opening.

The "interlabial space" refers to that space in the perineal region of the female anatomy which is located between the inside surfaces of the labia majora extending into the vestibule. Located within this interlabial space are the labia minor, the vestibule and the principal urogenital members including the clitoris, the orifice of the urethra (the urethral meatus), and the orifice of the vagina. The vestibule refers to the space bounded laterally by the inside surfaces of the labia minora and extending interiorly to the floor between the clitoris and the orifice of the vagina. The interlabial space may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

An "intermediate" layer refers to a layer between two others. In the embodiments disclosed herein the intermediate layer has a lower density than inner layer that faces the cavity and the outer layer that faces the exterior of the pad, so that the intermediate layer preferentially retains liquid (such as a bodily liquid) and acts as a reservoir for the liquid. In some embodiments the intermediate layer is also an anti-microbial layer so that microbial growth in the retained liquid is inhibited.

The term "labia" generally refers to both the labia majora and labia minora. The labia terminate anteriorly and posteriorly at the anterior commissure and the posterior commissure, respectively. Although there is a wide range of variation among women with respect to the relative size and shape of labia majora and labia minora, available morphometric data permits the manufacture of interlabial devices suited to fit in the interlabial space of the general population of women. In addition, such data permits different sizes of the devices to be made for different users, for example in pre-dimensioned sizes (such as small, medium and large). Placing the absorbent interlabial device into the interlabial space of a wearer involves placement between the inside surfaces of the labia majora without regard to the precise location of the boundary between the labia majora and the labia minora for a particular wearer.

A "non-adhesive" pad is a one that is configured to be retained without the use of an exogenous adhesive, such as an adhesive substance applied to the pad for the purpose of adhering the pad to the wearer and/or the wearer's garments. In one example, the "non-adhesive" pad does not have an adhesive surface on which an adhesive has been placed during manufacture of the pad. Alternatively the pad is not rendered adhesive, for example by chemical treatment or otherwise.

An "ovate" structure is one that has a generally egg-shaped cross-section. An ovate cross-section typically tapers between a broader end and a narrower end. Although the term "ovate" generally refers to a two-dimensional structure, the interlabial device disclosed herein is three-dimensional. The term ovate is only referring to a two-dimensional cross-section, without implying the absence of a third dimension in the structure.

The "perineum" is the anatomical space extending from the coccyx to the pubis and below the pelvic diaphragm. It includes the vulva and the anus in females, and the scrotum and the anus in males. A pad suitable for retention in the perineum is a pad that is of suitable dimensions to be held in the interlabial space or in an intergluteal space against the anus. Certain embodiments of the disclosed pad are suitable for retention against the external surface anatomy of the perineum, for example against the external surface of the anus or vaginal orifice, by retention within the intergluteal or interlabial spaces. The retention with these spaces can be achieved exclusively by frictional engagement or by pressure of the surrounding tissues on the pad to retain it in place, without the need for adhesive additives (such as exogenous surface adhesives) to secure the pad in position.

Figure 1:
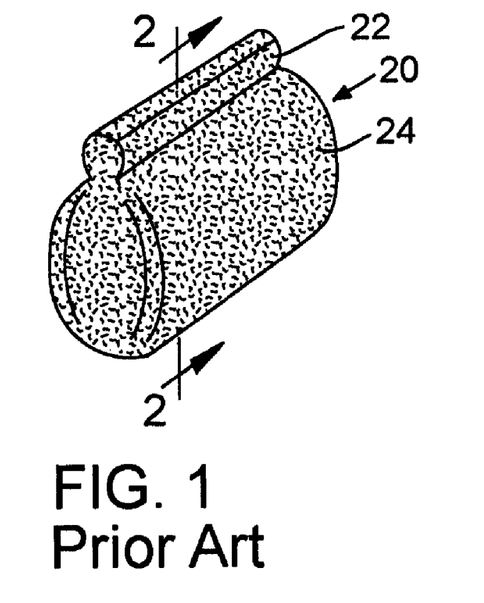
FIGS. 1 and 2 illustrate prior art interlabial pads, such as those shown in U.S. Pat. Nos. 3,983,873 and 4,175,561.
Figure 2:
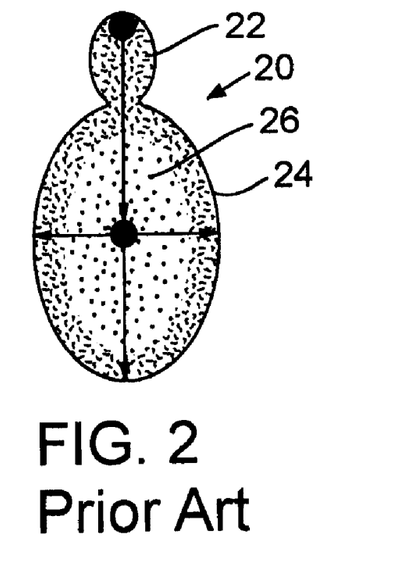

FIGS. 1 and 2 illustrate prior art interlabial pads of the type shown in U.S. Pat. Nos. 3,983,873 and 4,175,561. These pads are generally formed as a cylindrical rope that is compressed during the manufacturing process. The rope is stitched along one edge to divide the rope into a minor portion 22 (that is to be placed in the interlabial space against the body) and a major portion 24. The resulting elongated interlabial pad has an absorbent low density inner core 26 that extends along the length of the pad, and distributes collected liquid longitudinally through the pad. This configuration can in some instances promote the leakage of liquid (such as urine or menstrual fluid) from the ends of the pad during use. The collection of liquid in the inner core is also capable or promoting bacterial overgrowth, which can affect the outcome of a diagnostic assay. For example, if a quantitative assay is to be performed for the amount of bacteria in a specimen collected in the pad, the result of the assay can be affected by continued bacterial proliferation in the pad between the time of collection and the time of assay.

Some of these problems are addressed in the embodiment of the new interlabial device 28 shown in FIG. 3A. Device 28 is shown in cross-section, which is generally ovate (egg-shaped) in cross-section, with a broader top end 30 and a narrower bottom end 32. The device is formed from a pad that has multiple layers, such as the three layers shown in the drawing. These layers include an outer absorbent layer 34, an intermediate absorbent layer 36, and an inner absorbent layer 38 that are adhered directly to one another to form three contiguous layers. The terms "outer" and "inner" are used as relative terms that indicate the relationship of the layers to one another, and they do not necessarily require that the outer and inner layers be the outermost and innermost layers of the pad. Similarly, although the disclosed embodiment shows three layers that are contiguous to one another, other embodiments can use additional layers interposed between intermediate layer 36 and outer layer 34 or intermediate layer 36 and inner layer 38. In this disclosed embodiment, the intermediate layer also has anti-microbial properties and will therefore be referred to as an intermediate anti-microbial layer 36, although in other embodiments the intermediate layer is not anti-microbial.

A cavity 40 is present within the pad, and it can extend along the length of the device from end to end. The depicted embodiment of the partially-enclosed cavity 40 has open ends, although in other embodiments the ends may be closed to form a completely enclosed cavity. The illustrated cavity 40 is symmetric about an axis of symmetry (shown in dashed lines in FIGS. 3A and 3B). The cavity 40 is elongated in the direction of the axis of symmetry. Although not shown, cavity 40 is also elongated perpendicular to the illustrated axis of symmetry, so that it has two axes of elongation.

As shown in FIG. 3A, the rounded top of the pad is slightly compressed along the top line of the device so that layers 34, 36 and 38 have a reduced thickness in this region. The device is sealed along narrower end 32 of the elongated pad, for example by heat sealing, adhesive, or stitching of opposing longitudinal ends of the pad to one another. Since the pads are secured to one another along end 32 they constrain the width assumed by the pad in this region, however the less dimensionally constrained broader end 30 assumes a wider cross-sectional profile. This shape assists in retention of the pad in the interlabial space of the wearer. Hence this disclosed embodiment generally tapers in width from its top end to its bottom end. It is of course understood that in other embodiments the pad need not be made of a folded over pad having opposing edges sealed together; for example the pad can woven in contiguous concentric layers to form the multi-layered device. However, the illustrated folded pad embodiment is a particularly useful and simple means to manufacture the pad.

In the disclosed embodiment, absorbent layers 34, 38 are made of a spun polypropylene and intermediate layer 36 is a rayon (including variants such as acetate rayon) or silk, which have been found to have inherent anti-microbial activity. An example of an anti-microbial rayon suitable for use in the device is Photocatalyst Rayon available from Daiwabo Rayon Co., Ltd. However other rayon materials can be used, such as Rayon Lenzing 3.0 denier, type 8258; Rayon Carded Sliver (Steams Product Number W4482) from Steams Technical Textiles company; or Rayon Sliver from American Fiber and Finishing Company. The average fiber density of the rayon may be, for example, 0.001-0.1 g/cc, and in a particular example is about 0.01 g/cc. Alternatively the anti-microbial intermediate layer can be made of a material that lacks substantial inherent anti-microbial activity, but is treated with an anti-bacterial substance, such as an antibiotic or other anti-microbial substance (such as a coating of silver or the presence of colloidal silver or silver nitrate).

The antimicrobial/intermediate layer can have absorbent properties, but in some embodiments may be more or less absorbent than the absorbent layers. A "less absorbent" material is one that has a lesser capacity to absorb a liquid. The absorbent properties of a material can be determined, for example, by determining the time taken for a given volume of liquid to penetrate into the product. Examples of tests to make that determination are shown in U.S. Pat. No. 6,138,500. A material that has a faster liquid acquisition time in such a test is a more absorbent material.

The intermediate layer is preferably of a lower density than the absorbent layers between which it is sandwiched. The lower density of the intermediate layer allows it establish a liquid flow equilibrium in which the lower density material serves as a reservoir for liquid that is conveyed to it by the absorbent layers. The preferential retention of liquid in the intermediate lower density layer inhibits collection of liquid in the cavity that can then move along the length of the pad and out of its open ends. A ratio of the density (such as the average fiber density) of outer layer:intermediate layer:inner layer is about 1-1.5 to 0.25-0.5 to 1.75-2.25, for example about 1 to 0.25-0.4 to 2. In other embodiments, the density of the inner layer is about twice the density of the outer layer and at least twice the density of the intermediate layer.

In some disclosed examples, the thickness of the intermediate layer is greater than the thickness of the inner and outer layers to provide more of a reservoir for liquid to be retained in the intermediate layer. In other embodiments, the outer layer is of a substantially uniform thickness, the intermediate layer is of a substantially uniform thickness, and the inner layer is of a substantially uniform thickness. In some examples, a ratio of thicknesses (such as average thickness or maximum thickness) of the outer layer:intermediate layer: inner layer is about 0.5-1.5 to 8-12 to 1-2, for example about 1 to 10 to 1.5. The thickness of the intermediate layer is at least twice the thickness of the inner or outer layer, and in some embodiments is at least five times greater than the thickness of the inner or outer layer. Thicknesses of the layers in the drawings are not drawn to scale.

An example of the spun polypropylene absorbent material suitable for use in the highly absorbent inner and outer layers is polypropylene cover material in a hatch pattern, such as Veratec from Nonwovens Group, 100 Elm Street, Walpole Mass. 02081-1898. However other absorbent materials may be used. In certain embodiments that are to be used for collection of diagnostic material, it is preferred that non-super-absorbent materials be used to avoid damage to cellular structures in the collected liquid sample.

In use, device 28 is placed in a perineal (such as an interlabial) space of a user with broad end 50 against an anatomical orifice (such as the vaginal opening and/or urethral meatus), in the manner described in more detail below. Alternatively, the pad may be placed in the intergluteal space against the anus. After the pad is placed in position, surrounding tissue at least partially encloses device 28 and the device conforms to surrounding tissue. Pressure and/or friction supplied by the surrounding tissue retains device 28 in position, and can also at least partially collapse it, which in some embodiments partially reduces the volume of cavity 40. The pad collects liquid by absorbing it through outer absorbent layer 34 and wicking it to absorbent intermediate anti-microbial layer 36. The presence of the absorbent layers on each face of layer 36 helps direct liquid to layer 36. To the extent liquid is present in cavity 40, inner absorbent layer 38 directs it back into the pad. The internal cavity 40 in the pad of FIG. 3A is a potential space that is generally reduced in size or substantially eliminated when the pad is compressed by the body during use.

An alternative embodiment of a device 48 is shown in FIG. 3B which retains a broader end 50, narrower end 52, absorbent outer layer 54, intermediate anti-microbial layer 56, inner absorbent layer 58, and an internal cavity 60 that extends along the length of the pad. The layers of this embodiment of the device are less compressible, or folded across a greater angle, so that the thickness of the layers at end 50 is not reduced as in the embodiment of FIG. 3A. The volume of cavity 60 in its fully expanded state (prior to placement and compression by tissue) is therefore greater than in the embodiment of FIG. 3A. However device 50 is used and functions similarly to device 30.

Figure 4:
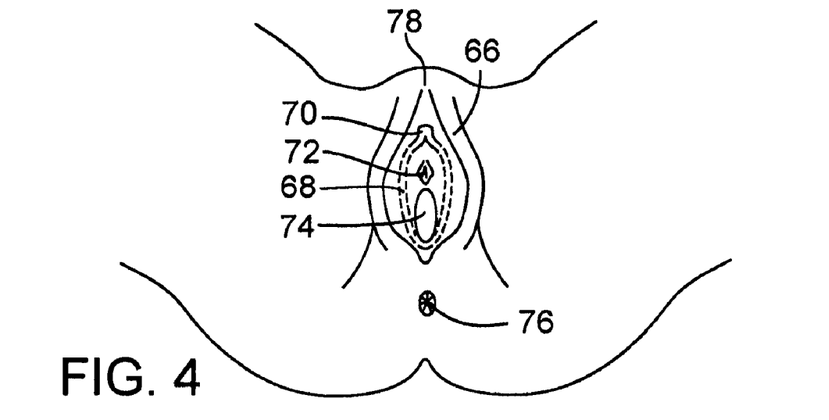
FIG. 4 is a schematic diagram illustrating the perineal anatomy, including labial and interlabial structures, of a human female.
Figure 5:
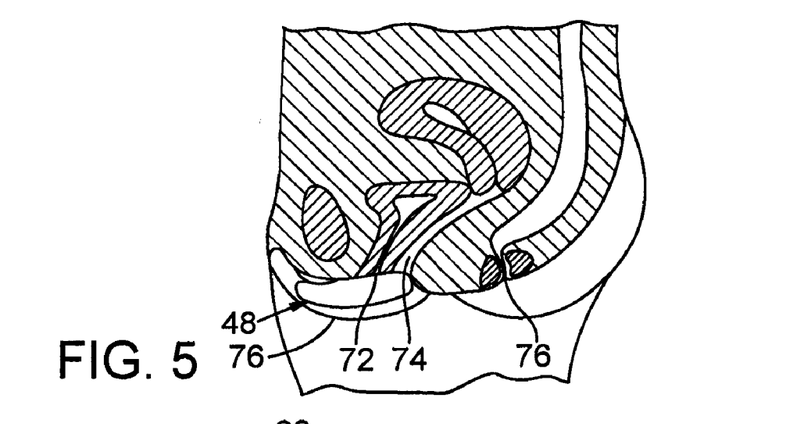
FIG. 5 is a schematic diagram illustrating a saggital midline cross-section of the pelvic anatomy of a human female.

FIG. 4 illustrates the female perineal anatomy. The drawing depicts the labia majora 66, labia minora 68, clitoris 70, urethral opening 72, vaginal orifice 74, anus 76 and mons pubis 78. FIG. 5 shows device 48 retained interlabially externally against the urethral opening 72 and vaginal opening 74 to absorb liquids from, or administer substances to, either orifice. In alternative embodiments (not shown), device 48 is positioned externally against anus 76 to absorb or administer substances at that orifice. "External" retention refers to retention (for example by the action of surrounding tissue) without placement into the vagina or anus.

Figures 6, 7:
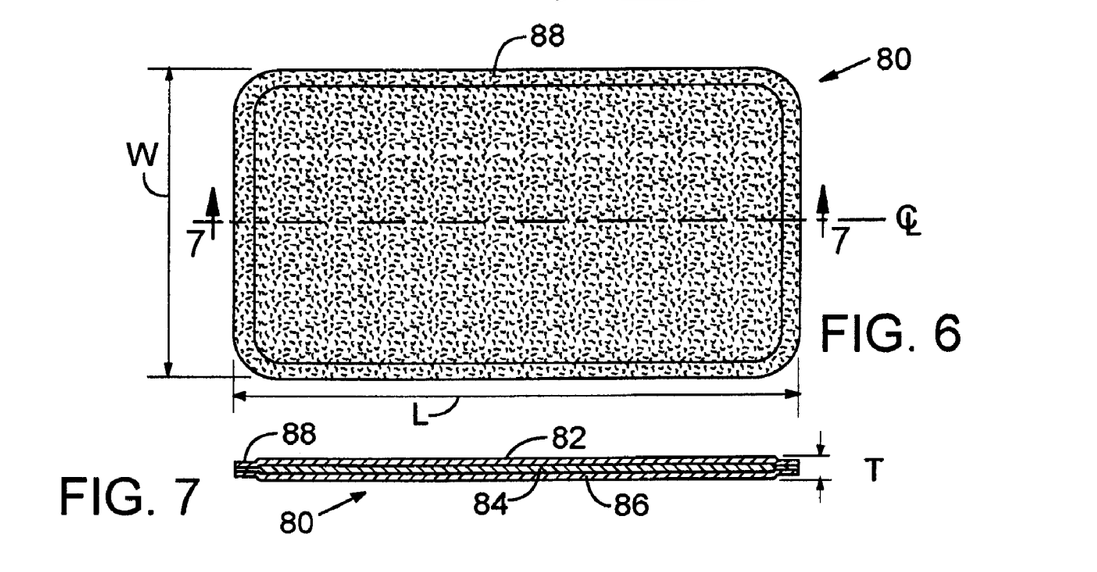
FIG. 6 is a front view of an absorbent pad for use in making the interlabial device disclosed herein.
FIG. 7 is a cross-sectional view taken along lines 7-7 of FIG. 6.

FIGS. 6-7 illustrate an embodiment of a pad 80 which is the starting material from which device 48 is made. Pad 80 has a length L, a width W, a thickness T, and a longitudinal centerline CL that extends the length of pad 80 and substantially bisects it into two generally symmetric portions on either side of centerline CL. The centerline CL need not be a geometric centerline, but rather serves functionally to divide pad 80 into the two generally symmetric portions. As shown in FIG. 7, pad 80 includes an outer absorbent layer 82, an intermediate (anti-microbial) layer 84, and an inner absorbent layer 86. Pad 80 is heat sealed around its outer edge to form a continuous compressed peripheral lip 88 having a reduced thickness compared to the main body of pad 80.

Figures 8A, 8B, 8C, 9A:
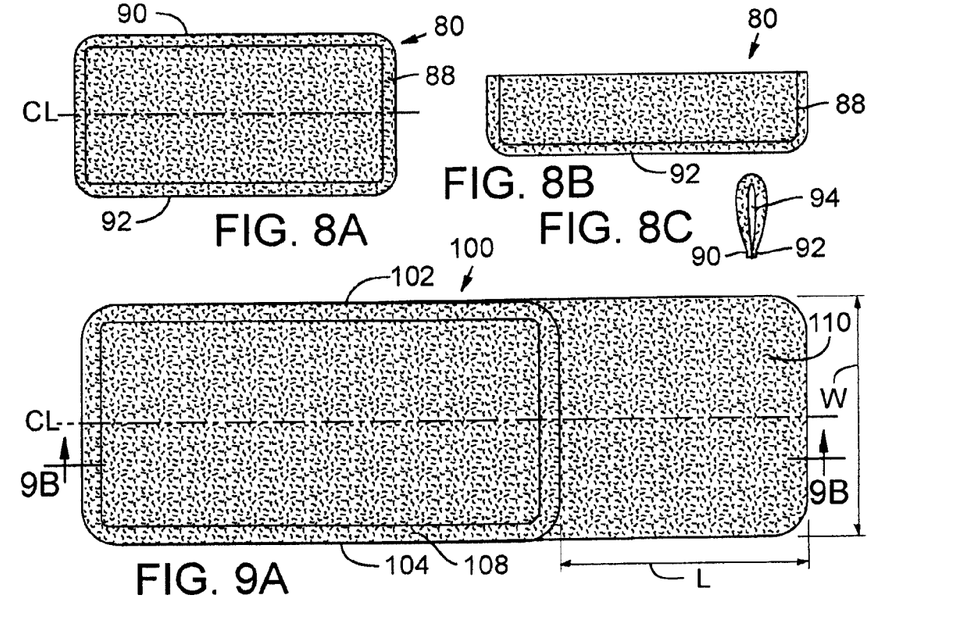
FIGS. 8A, 8B and 8C schematically illustrate the method of making the device by folding the pad along its longitudinal centerline and sealing the top and bottom edges of the pad to one another along a seam that becomes the bottom edge of the assembled pad.
FIG. 9A shows the embodiment of the pad that includes a flap extending from one transverse edge.

FIG. 8 illustrates a method of making the device from pad 80. As shown in FIG. 8A, pad 80 has opposing longitudinal edges that are arbitrarily designated top edge 90 and lower edge 92. Top and bottom edges 90, 92 are brought together by folding pad 80 along longitudinal centerline CL so that the height of pad 80 is substantially half the former height of the pad (FIG. 8B). Edges 90, 92 are then sealed to one another, for example by heat bonding, so that pad 80 assumes the general configuration shown in the end view of FIG. 8C in which pad 80 has a generally ovate cross-section that encloses a longitudinally extending cavity 94. The transverse ends of folded pad 80 are not sealed in the disclosed embodiment, but they may optionally be sealed to one another so that pad 80 forms an enclosed cavity 94.

FIG. 9 illustrates a method of making an alternative embodiment of the absorbent device. In this embodiment, pad 100 (FIG. 9A) is similar to pad 80 in that it is trilaminar, has a top edge 102 and bottom edge 104, and is substantially bifurcated by a longitudinal centerline CL. However pad 100 differs from pad 80 in that it has a flap 110 that is an extension of one of the absorbent layers (the outer absorbent layer in the embodiment of FIG. 9). This flap 110 is continuous with the absorbent layer, and has the same width W as the width of the main body of pad 100. The length of flap 110 in the illustrated embodiment is less than the length of the main body of pad 100, for example the length of flap 110 is about one-half the length L of the main body of the pad. Heat sealed peripheral lip 108 still extends around the generally rectangular pad 100, but not flap 110, such that flap 110 is separated from the main body of pad 100 by a heat seal that extends across the width of pad 100.

Figures 9B, 9C, 9D, 9E:
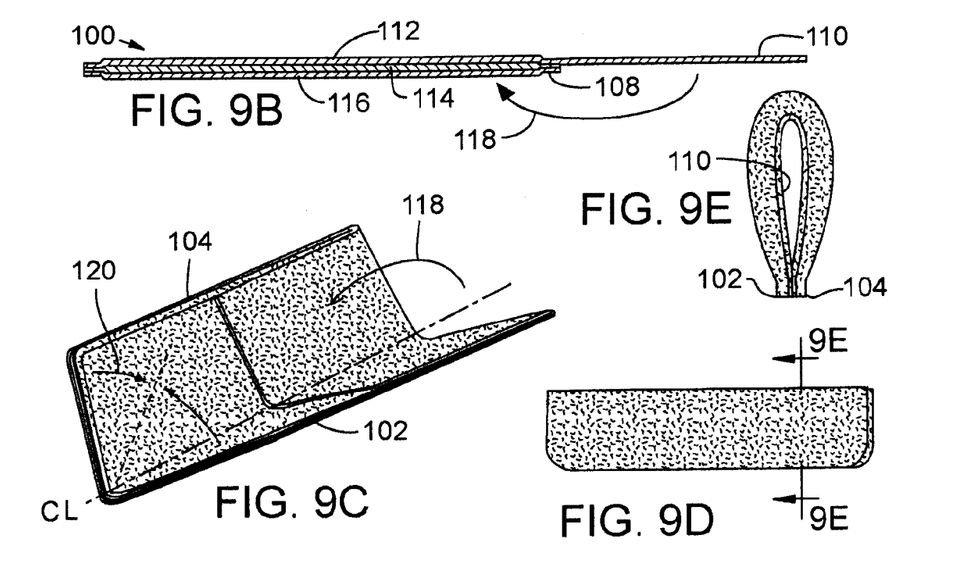
FIG. 9B is a cross-sectional view taken along line 9B-9B of FIG. 9A with the arrow illustrating that the flap is folded back against the main body of the pad.
FIG. 9C is a perspective view that illustrates the device after the flap is folded back against the pad but before the edges of the pad are sealed to one another.
FIG. 9D is a front elevational view of the pad after the flap is folded inside of it and the edges sealed together.
FIG. 9E is an enlarged cross-sectional view of the device along lines 9E-9E of FIG. 9D, showing the internal cavity of the device.

As shown in FIG. 9B, pad 100 includes an outer absorbent layer 112, intermediate layer 114 (which in this embodiment is anti-microbial), and inner absorbent layer 116. Flap 110 is an extension of outer layer 112 of pad 100, and flap 110 is folded (as illustrated by arrow 118) at heat sealed lip 108 over the lip and against inner face 116 until flap 110 is flat against inner face 116 as shown in FIG. 9C. Then pad 100 is again folded (as illustrated by arrow 120) along its longitudinal centerline CL to bring top and bottom edges 102, 104 together and heat seal them. The folded pad then has a front profile as shown in FIG. 9D, which is reduced in height from the unfolded pad. FIG. 9E is an enlarged cross-section of FIG. 9D which shows that edges 102, 104 have been sealed to one another to form an internal cavity. The end of the pad into which flap 110 has been folded is not shown in the drawing, but the folded flap helps soften that end of the pad by covering the sealed lip 108. The redundant material provided by the flap also provides a more diffuse edge that is less abrasive to body structures against which it is placed.

The manufacture of the device is simpler, more efficient and less expensive than manufacturing methods used for other pads. In addition, folding flap 110 over the heat sealed edge provides a softened leading edge of the device that can be positioned interlabially against the urethreal meatus to reduce potential irritation of this sensitive structure. In some embodiments the pad is non-adhesive, such that it does not adhere to the skin and/or a garment, for example it does not have an adhesive surface that adheres to the skin and/or a garment.

Use for Catamenial Purposes

The disclosed pad may be used for catamenial purposes, for example by placing the pad interlabially to absorb menstrual flow. The antibacterial intermediate layer of the pad inhibits the proliferation of bacteria in the pad during use.

Diagnostic Embodiments

In one embodiment, the pads are used to absorb discharge from the structures within the perineal space, for example from an interlabial structure such as the anus or (in a female) the urethral meatus, vagina, or vulvar epithelium. A diagnostic test is then performed on the absorbed discharge. In one embodiment, the discharge is a bodily liquid, such as blood or a secretion, such as a secretion derived from the reproductive system, including amniotic fluid and fetal fibronectin from the amniotic sac. In yet another embodiment, the discharge includes cells, such as cells of the vulvar, vaginal or cervical epithelium, and the cells are analyzed using a diagnostic test. The diagnostic test can be performed directly on the discharge absorbed by the pad, or the discharge or a component of the discharge can be extracted from the interlabial pad prior to performing the diagnostic test (see U.S. Pat. No. 5,094,956).

The diagnostic test can detect, for example, the presence or absence of a cell type (e.g. see U.S. Pat. No. 5,124,252; U.S. Pat. No. 5,965,375), a protein (e.g. see U.S. Pat. No. 5,190,881; U.S. Pat. No. 5,661,010), or a nucleic acid (e.g. see U.S. Pat. No. 5,538,851; U.S. Pat. No. 5,459,034) in a vaginal discharge. The diagnostic test can also be used to detect blood (see U.S. Pat. No. 4,920,045; U.S. Pat. No. 5,563,071), or the presence of a virus, such as human papillomavirus (HPV), or a microorganism, such as a pathogen (see U.S. Pat. No. 5,705,332; U.S. Pat. No. 5,627,275), or fetal fibronectin (indicating premature delivery), or fetal genetic material passed through the amniotic sac. The diagnostic test can be a qualitative, semi-quantitative, or quantitative test. In one specific, non-limiting example, the diagnostic test is used to detect a biological parameter associated with cervical cancer.

In a specific, non-limiting example, vaginal and vulvar discharge is collected on the pad and/or within the cavity inside the pad, and a diagnostic test is then performed on the discharge to detect human papillomavirus (HPV) infection. For example, the diagnostic test can detect the presence of HPV nucleic acid (see U.S. Pat. No. 5,580,907; U.S. Pat. No. 5,876,922; U.S. Pat. No. 5,783,412; U.S. Pat. No. 5,447,839; U.S. Pat. No. 5,283,171). Alternatively, the diagnostic test can detect the presence of a protein associated with HPV infection (see U.S. Pat. No. 5,045,447). The test can either be performed on the pad itself, or the discharge can be expressed from the pad and the test performed on the discharge. When the test is performed on the pad itself, diagnostic reagents can be added to the pad after the discharge is collected, or the pad can be supplied with a diagnostic reagent on or in the pad so that interaction with the discharge provides the test result. An example of a test result is a visible signal (such as a color change) that indicates the presence of a target analyte or pathogen that is to be detected by the test.

Therapeutic Embodiments

In another embodiment, a kit is provided for administering a therapeutic agent such as a medication from the drug delivery device. The kit includes an interlabial pad, and a package such as a plastic vial or a plastic or foil container, for packaging the interlabial pad. The kit can also include directions for the use of the pad. The pad can contain a unit dose of the medication, for example an anti-infective, such as GYNELOTRIMIN®. Another example is the delivery of estradiol to treat vaginal atrophy or for hormone replacement therapy (HRT). In HRT, an ILP system releasing 100 mg/day of estradiol as its 3-acetate ester maintains a circulating plasma concentration of 300 pmol/L of the drug, which is within the clinically desirable range for HRT.

Examples of other therapeutic agents that could be delivered using this system are the delivery of 20 micrograms/day ethinyl estradiol to hypoestrogenic subjects for peak bone mass acquisition during adolescence; 200 micrograms/day of 17.beta.-estradiol to relieve severe post-menopausal symptoms; 400 micrograms/day of the GnRH agonist nafarelin for 4 weeks in the initial treatment of endometriosis, followed by half-dose therapy (200 micrograms/day) for 20 weeks; local delivery of levofloxacin for the treatment of chlamydia trachomatis; or delivery of 1% flutrimazole for the treatment of fungal infections.

The therapeutic agent can be supplied either on the surface of the pad, impregnated into the material of which the pad is made, or provided in the cavity within the pad. The cavity of the pad provides a useful initial reservoir for the drug, and is therefore able to provide sustained administration of the therapeutic agent while the device is retained in position. Compression of the cavity by surrounding tissue during normal movements helps express the drug from the device to the target tissue. The absorbent inner and outer layers of the device establish a beneficial equilibrium that draws the drug out of the cavity so that it can reach the surrounding tissue, while inhibiting excess loss of the drug from the device. The absorbent equilibrium established by the absorbent but less dense intermediate layer can also control release of the drug to the environment. Embodiments of the pad in which the intermediate layer is an anti-microbial layer can protect the drug delivery device against the growth of pathogens either before or during use.

Anal Use

The disclosed absorbent pad can alternatively be positioned external to the anal orifice to collect any anal discharge. The pad can be retained in the intergluteal space, between the buttocks, without the use of a supporting garment or adhesive. Thus, in some embodiments the pad is non-adhesive, such that it does not adhere to the skin, for example it does not have an adhesive surface that adheres to the skin and/or a supporting garment. In particular embodiments, the pad is positioned external to the external anal sphincter, so that it is not retained by insertion in the anus but is instead retained by the pressure of the gluteal muscles or buttocks on the pad. For example the pad is retained in the intergluteal space and is not dislodged because the opposing right and left buttocks functionally close the gluteal cleft.

The pad is used in a method of absorbing anal leakage in a subject by positioning the absorbent pad between the buttocks, external to the subject's anal orifice, such that the pad is retained between and by the buttocks. In this position, any anal or peri-anal discharge is absorbed by the pad, which discharge may also be used for diagnostic testing purposes, such as for colon cancer. In particular embodiments, a method is disclosed for treating hemorrhoids by inserting the pad between the buttocks, against the external anal orifice.

The absorbent equilibrium that favors the movement of liquid to the intermediate layer is particularly advantageous when the intermediate layer is also an anti-microbial layer. The anti-microbial layer helps inhibit the growth of enteral bacteria. In addition, the intermediate layer can be provided with odor neutralizing agents.

In some embodiments, the method delivers therapeutic substances (such as antibiotics, topical anesthetics or topical vasoconstrictors), for example in the treatment of hemorrhoids. The method includes positioning the intergluteal pad such that the pad is retained between the buttocks external to the subject's anus. The top portion of the pad is designed for insertion of the pad between the subject's buttocks in the anatomic intergluteal space adjacent to the anus, and the bottom portion is retained between the buttocks without the need for adhesive (for example to adhere the device to the user's skin and/or undergarments) or other attachment devices. Insertion and retention of the pad adjacent to the anus alleviates one or more symptom of the hemorrhoids, or delivers drugs to the anal orifice.

Alternatively, the pad is retained against the anus to collect leakage of fecal material and avoid soiling of garments.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as the invention all that comes within the scope and spirit of these claims.

The invention claimed is:

1. A method of collecting biological liquid from a subject, comprising:
providing a multiple layer absorbent pad sized for retention in a perineal space of a wearer, the multiple layers of the pad comprising an inner absorbent layer, an outer absorbent layer, and an intermediate layer between the inner and outer absorbent layers, wherein the inner and outer absorbent layers are denser than the intermediate layer, and the pad forms an empty internal cavity within the pad, wherein liquid in the internal cavity is absorbed through the inner absorbent layer into the intermediate layer and liquid external to the device is absorbed through the outer absorbent layer into the intermediate layer; and
placing the pad in a perineal space of the wearer so that liquid is absorbed by the pad from the perineal space into the pad,
wherein the empty internal cavity is circumscribed in at least one plane by the inner absorbent layer and the intermediate layer circumscribes the inner absorbent layer in a continuous manner.

2. The method of claim 1, wherein the intermediate layer is an anti-microbial layer.

3. The method of claim 2, wherein the intermediate anti-microbial layer is treated with an antibacterial substance, or consists essentially of rayon or silk which have inherent anti-microbial activity.

4. The method of claim 3, wherein the intermediate anti-microbial layer consists essentially of rayon.

5. The method of claim 1, further comprising performing a diagnostic test of the liquid absorbed by the pad.

6. The method of claim 1, wherein the pad and cavity are elongated and generally taper in width from a top of the pad to a bottom of the pad, and a ratio of average fiber density of outer layer:intermediate layer:inner layer is about 1-1.5 to 0.25-0.5 to 1.75-2.25, and a ratio of thicknesses of outer layer:intermediate layer:inner layer is about 0.5-1.5 to 8-12 to 1-2.

7. The method of claim 1, wherein the pad is a folded pad that is sealed together along at least two opposing edges to form the internal cavity.

8. The method of claim 1, wherein the pad has an open end that communicates with the cavity, and the pad further comprises a flap that is folded from an edge of the pad into the cavity to form a protective layer.

9. The method of claim 1, wherein the pad has a generally ovate cross-section with an enlarged width top edge and a reduced width bottom edge, and the pad is placed in the perineal space with the enlarged width top edge against a body of the user.

10. The method of claim 1, further comprising:
transporting the collected biological liquid in the pad; and
extracting at least some of the collected biological liquid from the pad for diagnostic analysis.

11. A method of making a perineal absorbent pad for retention in a perineal space of a wearer, comprising:
providing an elongated multi-layered pad comprising at least one absorbent layer and an anti-microbial layer, the pad further comprising a length, a width, a thickness, a longitudinal centerline, and opposing top and bottom edges; and
folding the pad along the longitudinal centerline and securing the opposing top and bottom edges to one another to present the at least one absorbent layer externally of the anti-microbial layer, and the folded pad forms an internal longitudinal cavity that is surrounded by the pad in at least one plane;

wherein the at least one absorbent layer forms a continuous layer that circumscribes the cavity.

12. The method of claim 11, wherein the anti-microbial layer comprises a fiber that inhibits the growth of bacteria.

13. The method of claim 12, wherein the fiber that inhibits the growth of bacteria comprises rayon.

14. The method of claim 11, wherein the pad is folded so that the anti-microbial layer forms a non-external layer of the folded pad.

15. The method of claim 14, wherein the multi-layered pad comprises the anti-microbial layer between first and second absorbent layers, and the pad is folded so that first absorbent layer forms a wall of the internal cavity, the second absorbent layer forms an exterior of the pad, and the absorbent layer is between the absorbent layers.

16. The method of claim 11, wherein the pad is folded so that the external layer of the folded pad is non-adhesive.

17. The method of claim 11, wherein the at least one absorbent layer has a greater length than the anti-microbial layer so that the at least one absorbent layer forms a flap, and the flap is folded against the anti-microbial layer before folding the pad along the longitudinal centerline and securing the opposing top and bottom edges to one another, so that the flap forms an extra layer of the pad along a transverse open edge of the folded pad.

18. A device comprising:
a multiple layer absorbent pad sized for retention in a perineal space of a wearer, the multiple layers of the pad comprising an inner absorbent layer, an outer absorbent layer, and an intermediate layer between the first and second absorbent layers, wherein the inner and outer absorbent layers are denser than the intermediate layer; and
an internal cavity within the pad, wherein liquid in the internal cavity is absorbed through the inner absorbent layer into the intermediate layer and liquid external to the device is absorbed through the outer absorbent layer into the intermediate layer, and the greater density of the inner and outer layer results in liquid flow that favors retention of the liquid in the intermediate layer instead of the cavity within the pad,
wherein the cavity is circumscribed in a two-dimensional cross-section by the inner absorbent layer and the intermediate layer circumscribes the inner absorbent layer in a continuous manner.

19. The device of claim 18 wherein the inner absorbent layer is an innermost layer of the device that is exposed to and forms the cavity within the device, and the outer absorbent layer is an outermost layer of the pad.

20. The device of claim 19, wherein the anti-microbial layer contains an added anti-microbial agent.

21. The device of claim 18, wherein the intermediate layer is an anti-microbial layer.

22. The device of claim 21, wherein the anti-microbial layer comprises a fiber that inhibits the growth of bacteria.

23. The device of claim 22, wherein the fiber that inhibits the growth of bacteria comprises a rayon or silk material.

24. The device of claim 18, wherein a ratio of the average fiber density of outer layer:intermediate layer:inner layer is about 1-1.5 to 0.25-0.5 to 1.75-2.25 and a ratio of thicknesses of the outer layer:intermediate layer:inner layer is about 0.5-1.5 to 8-12 to 1-2.

25. The device of claim 18, wherein the multiple layer absorbent pad has a length, a width, a thickness, a longitudinal centerline, and opposing top and bottom edges, wherein the pad is folded along the longitudinal centerline with the opposing top and bottom edges secured to one another to present the at least one absorbent layer externally of the intermediate layer, and the folded pad forms an internal cavity.

26. The device of claim 18, further comprising a flap extending from a transverse edge of the absorbent pad, wherein the flap is folded against the pad so that the flap is contained within the internal cavity.

27. The device of claim 26, wherein the flap is an extension of the absorbent layer.

28. The device of claim 18, wherein the pad is a pad that is folded along a folding line, and tapers in transverse cross-sectional profile away from the folding line.

29. The device of claim 18, wherein the pad is non-adhesive.

30. The device of claim 18, wherein the pad has substantially smooth outer surfaces.

31. A method for collecting fluid and/or exfoliated cells contained in the fluid from a perineal orifice for diagnostic purposes, the method comprising:
placing in a perineal space the device of claim 18;
collecting fluid in the device while the device is located in the perineal space;
removing the device from the perineal space;
extracting fluid from the device; and
performing medical diagnostic testing on the extracted fluid.

32. The method of claim 31, wherein the perineal space is an interlabial space.

33. The method of claim 32, wherein the extracted fluid contains cells comprising one or more of ectocervical, cervical, endometrial, vaginal or blood cells.

34. The method of claim 31, wherein the perineal space is an intergluteal space adjacent to and external of the anus.

35. The method of claim 31, wherein the diagnostic testing is directed to organisms and biological material associated with bacterial, viral and parasitic diseases.

36. The method of claim 31, wherein the diagnostic testing is directed to biological materials associated with cancers.

37. The method of claim 31, further comprising the step of placing the absorbent media into a shipping container prior to extracting fluid from the absorbent media.

38. A method of using the pad of claim 18 to administer a therapeutic agent to a subject, comprising:
providing a therapeutic agent in the pad; and
inserting the pad into a perineal space where it is retained to administer the therapeutic agent to the subject.

39. The method of claim 38, wherein inserting the pad into the perineal space comprises inserting the pad into an interlabial space or an into an intergluteal space against an anus.

40. The method of claim 38, wherein providing a therapeutic agent in the pad comprises placing the therapeutic agent in the cavity.

* * * * *

UNITED STATES PATENT AND TRADEMARK OFFICE
CERTIFICATE OF CORRECTION

PATENT NO.        : 8,398,606 B2
APPLICATION NO.   : 12/529053
DATED             : March 19, 2013
INVENTOR(S)       : William H. Fleming It is certified that error appears in the above-identified patent and that said Letters Patent is hereby corrected as shown below:

On the Title Page, item "(73) Assignee: QuantrRx Biomedical Corporation, Portland, OR (US)"

should read - (73) Assignee: QuantRx Biomedical Corporation, Portland OR (US) -

Signed and Sealed this
Eighteenth Day of November, 2014

Michelle K. Lee
*Deputy Director of the United States Patent and Trademark Office*